United States Patent
Rousseau et al.

[11] 4,093,720
[45] June 6, 1978

[54] NOVEL-17-SPIROSULTINES THEIR CORRESPONDING HYDROXY ACIDS AND COMPOSITIONS THEREOF

[75] Inventors: Geneviève Rousseau, Paris; Vesperto Torelli, Maisons-Alfort, both of France

[73] Assignee: Roussel Uclaf, Paris, France

[21] Appl. No.: 776,942

[22] Filed: Mar. 14, 1977

[30] Foreign Application Priority Data

Mar. 16, 1976   France .............................. 76 07476

[51] Int. Cl. .................... C07j 33/00; C07j 21/00; A61k 31/58
[52] U.S. Cl. ................ 424/241; 260/239.55 R; 260/397.4; 260/397.5
[58] Field of Search ............. 260/239.55, 397.4, 397.5

[56] References Cited

U.S. PATENT DOCUMENTS 3,971,777   7/1976   Rousseau et al. ................... 424/241

*Primary Examiner*—Elbert L. Roberts
*Attorney, Agent, or Firm*—Hammond & Littell

[57] ABSTRACT

Novel 17-spirosultines and their corresponding γ-hydroxy acids of the formula

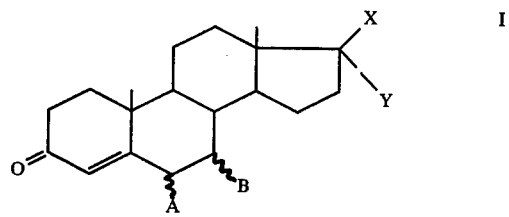

wherein A is hydrogen and B is alkyl of 1 to 4 carbon atoms in the α- or β-position or A and B form a methylene group in the 6α, 7α- or 6β, 7β-position and X and Y form a group of the formula

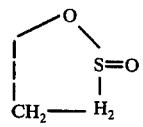

or X is OH and Y is

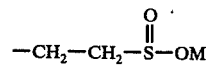

and M is selected from the group consisting of hydrogen, —NH$_4$ and an alkali metal cation having antialdosterone activity and their preparation and novel intermediates therefore.

15 Claims, No Drawings

NOVEL-17-SPIROSULTINES THEIR CORRESPONDING HYDROXY ACIDS AND COMPOSITIONS THEREOF

STATE OF THE ART

U.S. Pat. No. 3,971,777 discloses 17-spirosultines of steroids having antialdosterone activity.

OBJECTS OF THE INVENTION

It is an object of the invention to provide the novel steroids of formula I and to provide a novel process and novel intermediates for their preparation.

It is another object of the invention to provide novel antialdosterone compositions.

It is an additional object of the invention to provide a novel method of treating arterial hypertension and cardiac insufficiency in warm-blooded animals.

These and other objects and advantages of the invention will become obvious from the following detailed description.

THE INVENTION

The novel compounds of the invention are 17-spirosultines and their corresponding γ-hydroxy acids of the formula

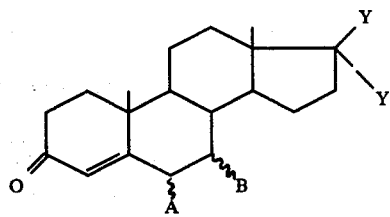

wherein A is hydrogen and B is alkyl of 1 to 4 carbon atoms in the α- or β-position or A and B form a methylene group in the 6α, 7α- or 6β, 7β-position and X and Y form a group of the formula

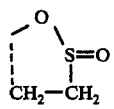

or X is OH and Y is

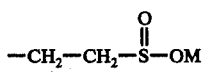

and M is selected from the group consisting of hydrogen, —NH₄ and an alkali metal cation.

The compounds exist in the form of 2 diastereoisomers about the sulfur atom which can be separated and which are denominated as isomer A and isomer B by convention with the isomer A being the isomer with the higher melting point.

When B is an alkyl, it is preferably methyl, ethyl, n-propyl or n-butyl. When M is an alkali metal cation, it is preferably lithium, sodium or potassium.

The compounds of the invention of formula I have X and Y forming the group

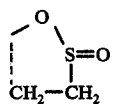

as well as X being OH and Y being

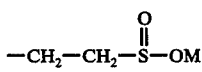

and M is —NH₄, hydrogen or an alkali metal cation. Also among the compounds of formula I are those where A and B form a methylene group in 6α, 7α or 6β, 7β-position and those where A is hydrogen and B is alkyl of 1 to 4 carbon atoms in the 7α-position and especially those where B is 7α-methyl.

The novel process of the invention for the preparation of a compound of formula I wherein X and Y form the group

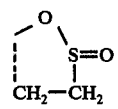

comprises reacting a compound of the formula

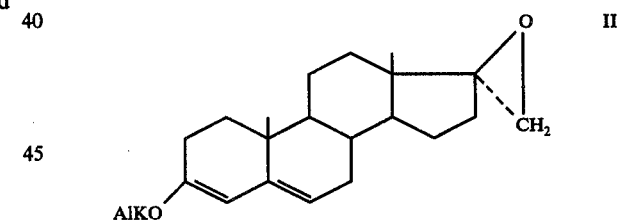

wherein AlK is alkyl of 1 to 4 carbon atoms with methyl tert.-butyl sulfoxide in the presence of n-butyllithium to obtain a compound of the formula

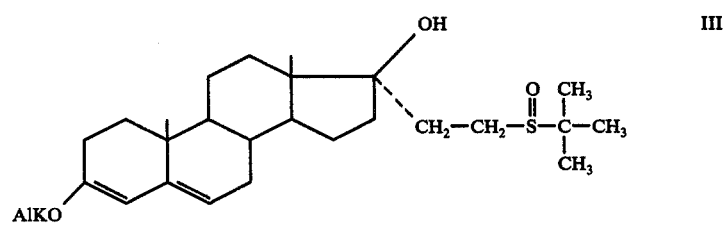

in the form of a mixture of diastereoisomers A and B about the sulfur atom, which may be separated if desired, reacting the latter with a dehydrogenation agent to form a compound of the formula

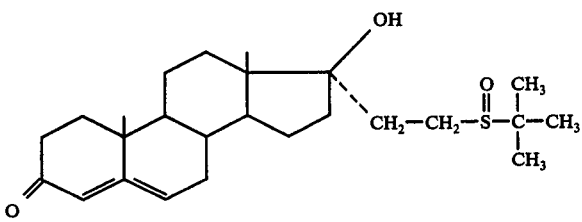
IV in the form of a mixture of diastereoisomers A and B which may be separated or as the individual isomer and either reacting the latter with a member of the group consisting of trimethylsulfonium iodide and trimethylsulfoxonium iodide in the presence of a strong base to obtain a compound of the formula

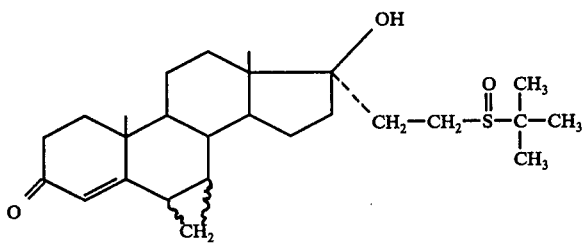
V in the form of a mixture of 6α, 7α- and 6β, 7β-isomers which may be separated if desired or reacting the compound of formula IV with a dialkylcuprolithium of the formula (AlK')$_2$—CuLi wherein AlK' is alkyl of 1 to 4 carbon atoms to form a compound of the formula

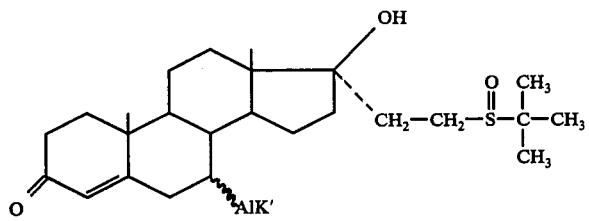
VI in the form of a mixture of 7α- and 7β-isomers which may be separated if desired and then reacting a compound of formulae V or VI with a member of the group consisting of N-chlorosuccinimide and N-bromosuccinimide to form a compound of the formula

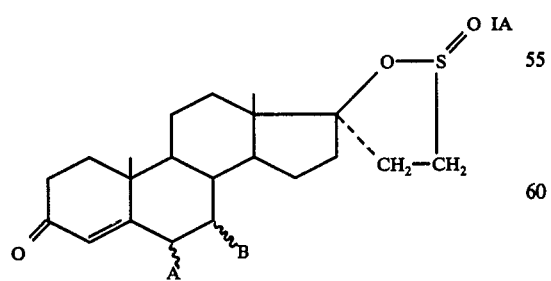
IA wherein A and B have the above definition.

In a variation of the process of the invention, a compound of formula IV in the form of its diastereoisomer mixture or its individual isomer A or B is reacted with an alkyl magnesium halide of 1 to 4 alkyl carbon atoms in the presence of a cuprous salt to obtain a compound of formula VI in the form of a mixture of the 7α- and 7β-isomers.

In the preferred mode of the invention the group AlK is methyl, ethyl, n-propyl or n-butyl and the dehydrogenation agent is preferably chloranil but equally useful are other derivatives of p-benzoquinone such as 2,3-dichloro-5,6-dicyanobenzoquinone. The strong base to form the corresponding ylide of trimethylsulfonium iodide or trimethylsulfoxonium iodide is preferably sodium hydride or potassium tert.-butylate. The preferred dialkylcuprolithium is dimethylcuprolithium and the preferred cyclization agent of the sultine is N-chlorosuccinimide.

The alkyl magnesium halide is preferably the chloride, bromide or iodide such as n-propyl magnesium bromide. The cuprous salt may be cuprous bromide, cuprous iodide or cuprous chloride, for example. When an alkyl magnesium halide is used, it is preferable to block the 17-hydroxy group of formula IV such as with dihydropyran. The separation of the diastereoisomers may be effected by known methods such as chromatography or crystallization.

The process of the invention for the preparation of compounds of formula I wherein X is OH and Y is

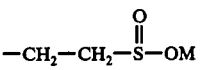

and M is hydrogen, —NH$_4$ or an alkali metal cation comprises reacting a compound of formula IA with either ammonium hydroxide or an alkali metal hydroxide to obtain the corresponding compound of formula I wherein M is —NH$_4$ or an alkali metal cation and the latter may be treated with an acidification agent to obtain the compound of formula I wherein M is hydrogen and if desired the acid may be treated with an alkali metal base to obtain the corresponding alkali metal salt of formula I.

In a variation of the process of the invention to produce a compound of formula I wherein B is alkyl of 1 to 4 carbon atoms, a compound of the formula

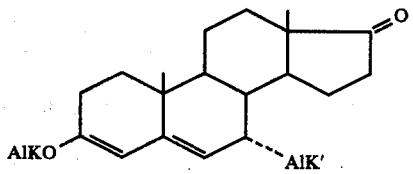
VII wherein AlK and AlK' have the above definition is reacted with trimethylsulfonium iodide or trimethylsulfoxonium iodide in the presence of a strong base to obtain a compound of the formula

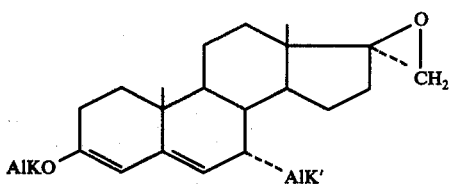
VIII and the latter is reacted with methyl tert.-butyl sulfoxide in the presence of n-butyllithium and then with an acid to obtain a compound of the formula

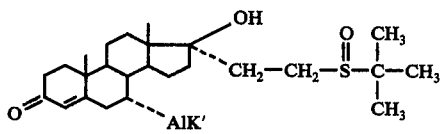
VI$_A$ in the form of a mixture of the diastereoisomers about the sulfur atom, which may be separated if desired, and the said product is reacted with thionyl chloride, N-chlorosuccinimide or N-bromosuccinimide to obtain a compound of the formula

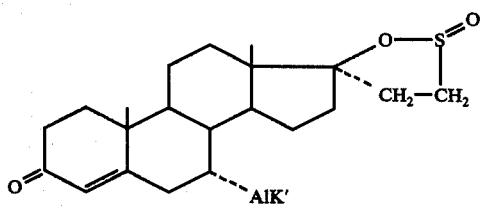

in the form of a diastereoisomer or a mixture of diastereoisomers which can be separated if desired.

The strong base is preferably sodium hydroxide, potassium hydroxide or potassium tert.-butylate. The acid is preferably hydrochloric acid, sulfuric acid, acetic acid or p-toluene sulfonic acid.

The novel intermediate products of the invention are those of formulae III, IV, V, VI and VIII.

The starting compounds of formula II are generally known and may be prepared by the process of Belgium Pat. No. 810,644 wherein a compound of the formula

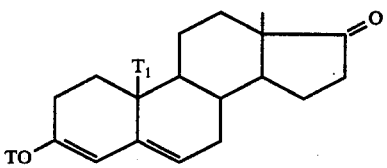

wherein T is methyl or ethyl and $T_1$ is hydrogen or methyl is reacted in the presence of a base with a trimethylsulfonium halide of the formula

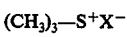
$(CH_3)_3-S^+X^-$ wherein X is bromine or iodine to obtain a compound of the formula

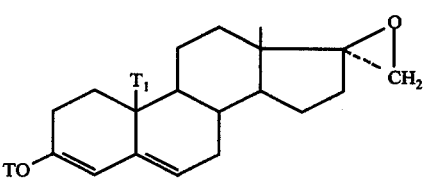

The compounds of formula VII, also used as starting materials, are generally known and may be made by the process of U.S. Pat. No. 3,383,282.

The novel antialdosterone compositions of the invention which increase hydrosodium diuresis while conserving organic potassium are comprised of an antialdosteronically effective amount of at least one compound of formula I and an inert pharmaceutical carrier or excipient. The compositions may be in the form of tablets, coated tablets, cachets, capsules, granules, emulsions, syrups, suppositories and injectable solutions or suspensions.

Examples of suitable excipients for the compositions are talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, dispersants and emulsifiers.

The compositions of the invention differ advantageously from other antialdosterone agents in that they present a negligeable or null relative affinity for androgen receptors which permits use of the compositions without side effects in which these receptors are implied, that are the side effects of androgen and antiandrogen type. The compositions are therefore useful for the treatment of arterial hypertension and cardiac insufficiencies.

The novel method of the invention for relieving hypertension and cardiac insulfficiencies in warm-blooded animals, including humans, comprises administering to warm-blooded animals a hypotensively effective amount of at least one compound of formula I. The compounds may be administered orally, rectally, transcutaneously or intraveinously. The usual useful dose is 2 to 20 mg/kg depending upon the compound and the method of administration.

In the following examples there are described several preferred embodiments to illustrate the invention. However, it is to be understood that the invention is not intended to be limited to the specific embodiments.

EXAMPLE 1 isomer B of (17R) 6β, 7β-methylene-2'-oxidospiro (Δ⁴-androstene-17,5'-[1',2']-oxathiolane)-3-one and isomer B of (17R) 6α, 7α-methylene-2'-oxidospiro (Δ⁴-androstene-17,5'-[1',2']-oxathiolane)-3-one STEP A: 3-ethoxyspiro-17β-oxiranyl-Δ³,⁵-androstadiene A suspension of 45.2 g of sodium hydride in 1500 of dimethylsulfoxide was heated at 60° C for 2 hours and then stood overnight at room temperature. Then, 1200 ml of tetrahydrofuran were added to the resulting black solution and after cooling the mixture to −5° C, a suspension of 384 g of trimethylsulfonium iodide in 1350 ml of dimethylsulfoxide was added thereto. A solution of 150 g of 3-ethoxy-Δ³,⁵-androstadiene-17-one [prepared from Δ⁴-androstene-3,17-dione as described by Serini et al, Ber., Vol. 71 (1938), p. 1766] in 1200 ml of tetrahydrofuran was added to the mixture at −5° C and after returning to room temperature, the mixture was stirred for 17 hours. The mixture was poured into 15 liters of ice water and after stirring for one hour, the mixture was vacuum filtered. The recovered precipitate was washed with water, dried and crystallized from acetone to obtain 139.7 g of 3-ethoxyspiro-17β-oxiranyl-Δ³,⁵-androstadiene in the form of colorless crystals melting at 105° C and having a specific rotation of $[\alpha]_D^{20} = -161°$ (c = 1% in ethanol containing 1% of pyridine).

Analysis: $C_{22}H_{32}O_2$; Calculated: %C 80.44 %H 9.82; Found: 80.5 10.0.

STEP B: isomers A and B of 3-ethoxy-21-tertbutylsulfinyl-Δ³,⁵-(17α)-pregnadiene-17-ol 145 ml of a solution of 2M of n-butyllithium in cyclohexane were added over 45 minutes under a nitrogen current at 5° C to a mixture of 34.8 g of tert.-butyl sulfoxide and 500 ml of tetrahydrofuran and then 38 g of 3-ethoxyspiro-17β-oxiranyl-Δ³,⁵-androstadiene were added thereto. After 15 hours at room temperature, the mixture was diluted with water and was extracted with ethyl acetate. The organic phase was dried and evaporated to dryness under reduced pressure to obtain 52.3 g of dry product. The product was chromatographed under high pressure over a column of 1.6 kg of Kieselgel H and was eluted with an 8-2 benzene-acetone mixture to obtain 18.05 g of 3-ethoxy-21-tertbutylsulfinyl-Δ³,⁵-(17α)-pregnadiene-17-ol melting at 200°-205° C (isomer A).

Analysis: $H_{27}H_{44}O_3S$; molecular weight = 448.714; Calculated: %C 72.27 %H 9.88 %S 7.14; Found: 72.2 9.9 7.1.

Elution with a 1:1 benzene-acetone mixture yielded 20.35 g of the isomer B with a melting point at 140° C and then 180° C.

Calculated: %C 72.27 %H 9.88 %S 7.14; Found: 71.9 9.7 7.0.

STEP C: isomer A of 21-tertbutylsulfinyl-Δ⁴,⁶-(17α)-pregnadiene-17-ol-3-one 5.3 g of chloranil were added to a solution of 8.2 g of isomer A from Step B in 320 ml of acetone containing 10% water and the mixture was stirred for 4½ hours at room temperature and was then poured into water. The mixture was extracted with ethyl acetate and the extracts were washed, dried and evaporated to dryness to obtain 3.1 g of residue. The combined mother liquors and wash waters were saturated with sodium chloride and were extracted with chloroform to recover another 4.3 g of residue. The 7.4 g of residue was chromatographed over silica gel and was eluted with a 6-4 benzene-acetone mixture to obtain 6.7 g of 21-tertbutylsulfinyl-Δ⁴,⁶-(17α)-pregnadiene-17-ol-3-one (isomer A) melting at 260° C after crystallization from isopropanol.

STEP D: isomer B of (17R) 6β, 7β-methylene-2'-oxidospiro-(Δ⁴-androstene-17,5'-[1',2']-oxathiolane)-3-one and isomer B of (17R) 6α, 7α-methylene-2'-oxidospiro-(Δ⁴-androstene-17,5'-[1',2']-oxathiolane)-3-one 6.6 g of trimethylsulfoxonium iodide were added under nitrogen to a suspension of 1.2 g of sodium hydride in 57% oil and 60 ml of tetrahydrofuran and 2.2 g of the product of Step C were added over 25 minutes. The reaction mixture was heated at 55° C for 3 hours and was then stirred overnight at room temperature. The mixture was poured into ice-water and was extracted with chloroform. The organic extracts were washed with water, dried over sodium sulfate and evaporated to dryness. The residue was dissolved in 60 ml of tetrahydrofuran and 30 ml of water and 780 mg of N-chlorosuccinimide were added thereto. After 15 minutes, the tetrahydrofuran was evaporated. The gum was separated and was extracted with chloroform. The organic phase was dried and distilled to dryness. The residue was chromatographed over silica gel and was eluted with a 1-1 benzene-ethyl acetate mixture to obtain 350 mg of (17R) 6α, 7α-methylene-2'-oxidospiro-(Δ⁴-androstene-17,5'-[1',2']-oxathiolane)-3-one melting at 200° C after crystallization from a ethyl acetate-isopropyl ether mixture with a specific rotation $[\alpha]_D^{20} = +37° \pm 2.5°$ (c = 0.5% in chloroform) and then 800 mg of (17R) 6β, 7β-methylene-2'-oxidospiro-(Δ⁴-androstene-17,5'-[1',2']-oxathiolane)-3-one melting at 208° C after crystallization from ethyl acetate and a specific rotation $[\alpha]_D^{20} = 247.5° \pm 3.5°$ (c = 1% in chloroform).

EXAMPLE 2 isomer B of (17R) 7α-methyl-2-oxidospiro-(Δ⁴-androstene-17,5'-[1',2']-oxathiolane)-3-one STEP A: 3-ethoxy-7α-methyl-spiro-Δ³,⁵-(17R)-androstadiene-17,2'-oxirane A mixture of 4 g of potassium tertbutylate in 30 ml of dimethylsulfoxide was stirred under nitrogen for 15 minutes at 60° C and after cooling to −5° C, 20 ml of tetrahydrofuran and 6.4 g of trimethylsulfonium iodide were added to the solution. The mixture was stirred for 10 minutes at −5° C and a solution of 5.5 g of 3-ethoxy-7α-methyl-Δ³,⁵-androstadiene17-one (prepared by process of U.S. Pat. No. 3,383,282) in 35 ml of tetrahydrofuran was added thereto. The temperature of the mixture returned to room temperature and after 30 minutes, the mixture was poured into an ice-water mixture. The mixture was stirred for 10 minutes and was vacuum filtered. The product was washed with water and dried to obtain 5.7 g of 3-ethoxy-7α-methyl-spiro-Δ³,⁵-(17R)-androstadiene-17,2'-oxirane melting at 146° C which was used as is for the next step.

STEP B: isomer A of (17R) 7α-methyl-21-tertbutylsulfinyl(17α)-Δ⁴-pregnene-17-ol-3-one 20.5 ml of a solution of 2M n-butyllithium in hexane were added at 5° C over 15 minutes to a solution of 4.9 g of tertbutylmethyl sulfoxide in 70 ml of tetrahydrofuran and after 10 minutes, 5.6 g of the product of Step A in 20 ml of tetrahydrofuran were added thereto. The temperature of the mixture returned to room temperature to obtain a limpid solution which was stirred overnight. The mixture was poured into an ice-water mixture and was extracted with methylene chloride. The extracts were washed with water, dried over sodium sulfate and evaporated to dryness to obtain 7.3 g of product. The latter was dissolved in 70 ml of acetone and 10 ml of 2N hydrochloric acid. After 15 minutes, the mixture was diluted with water and was vacuum filtered to obtain 6.3 g of a mixture of isomers. The product was chromatographed over silica and was eluted with an 80-20 chloroform-acetone mixture to obtain 2.5 g isomer A of (17R) 7α-methyl-21-tertbutyl-sulfinyl-$\Delta^4$-(17α)-pregnene-17-ol-3-one melting at 270° C after crystallization from a methylene chloride-methyl ethyl ketone and a specific rotation $[\alpha]_D^{20}$ = −15.5° ± 1.5° (c = 0.75% in chloroform) and then 2.5 g of isomer B of (17R) 7α-methyl-21-tertbutylsulfinyl-$\Delta^4$-(17α)-pregnene-17-ol-3-one melting at 248° C after crystallization from a methyl ethyl ketone-isopropyl ether mixture and a specific rotation $[\alpha]_D^{20}$ = +108.5° ± 2° (c = 0.85% in chloroform).

STEP C: isomer B of (17R) 7α-methyl-2-oxidospiro-($\Delta^4$-androstene-17,5'-[1',2']-oxatiolane)-3-one 680 mg of N-chlorosuccinimide were added to a suspension of 2.3 g of isomer A of Step B, 30 ml of tetrahydrofuran and 15 ml of water and the mixture was held at room temperature for 30 minutes and was then diluted with water. The tetrahydrofuran was evaporated and the mixture was vacuum filtered. The recovered crystals were washed and dried to obtain 1.8 g of product which was dissolved in 10 ml of refluxing ethyl acetate. The mixture was filtered and the filtrate was concentrated to 4 ml. 4 ml of isopropyl ether were added thereto and the mixture was vacuum filtered. The recovered crystals were washed and dried to obtain 1.33 g of the B isomer of (17R) 7α-methyl-2-oxidospiro-($\Delta^4$-androstene-17,5'-[1',2']-oxathiolane)-3-one melting at 180° C and having a specific rotation $[\alpha]_D^{20}$ = + 14° ± 2° (c = 0.5% in chloroform).

EXAMPLE 3

B isomers of (17R) 7α-methyl-2-oxidospiro-($\Delta^4$-androstene-17,5'-[1',2']-oxathiolane)-3-one and (17R) 7β-methyl-2-oxidospiro-($\Delta^4$-androstene-17,5'-[1',2']-oxathiolane)-3-one STEP A: A isomers of 7α-methyl-21-tertbutylsulfinyl-$\Delta^4$-(17α)-pregnene-17-ol-3-one and 7β-methyl-21-tertbutylsulfinyl-$\Delta^4$-(17α)-pregnene-17-ol-3-one 15 ml of a solution of 1.5N methyllithium in ether were added at 0° C under nitrogen to a mixture of 2.2 g of cuprous iodide and 40 ml of anhydrous ether and then a solution of 420 mg of the A isomer of 21-tertbutylsulfinyl-$\Delta^{4,6}$-(17α)-pregnadiene-17-ol-3-one in 25 ml of anhydrous tetrahydrofuran were added thereto at −10° C. The solution was held at 10° C for 30 minutes and was then poured into 30 ml of 2N hydrochloric acid. The mixture was filtered and 20 ml of 5N hydrochloric acid were added to the filtrate.

The mixture was stirred for one hour and the aqueous phase was saturated with ammonium sulfate. The mixture was extracted with ethyl acetate and the extracts were dried over sodium sulfate and evaporated to dryness to obtain 600 mg of product. The latter was chromatographed over silica gel and was eluted with a 7-3 chloroform-acetone mixture to obtain 240 mg of a mixture of the A isomers of 7α-methyl-21-tertbutylsulfinyl-$\Delta^4$-17α-pregnene-17-ol-3-one and 7β-methyl-21-tertbutylsulfinyl-$\Delta^4$-17α-pregnene-17-ol-3-one.

STEP B: B isomers of (17R) 7α-methyl-2'-oxidospiro-($\Delta^4$-androstene-17,5'-[1',2']-oxathiolane)-3-one and (17R) 7β-methyl-2'-oxidospiro-($\Delta^4$-androstene-17,5'-[1',2']-oxathiolane)-3-one 60 mg of N-chlorosuccinimide wre added to a suspension of 190 mg of the product of Step A, 2.5 ml of water and 3.5 ml of tetrahydrofuran and the solution was stirred for 30 minutes. The tetrahydrofuran was evaporated and the mixture was extracted with ethyl acetate and the extracts were dried over sodium sulfate and evaporated to dryness to obtain 162 g of a mixture of the B isomers of (17R) 7α-methyl-2-oxidospiro-($\Delta^4$-androstene-17,5'-[1',2']-oxathiolane)-3-one and (17R) 7β-methyl-2-oxidospiro-($\Delta^4$-androstene-17,5'-[1',2']-oxathiolane)-3-one. The said 7α-methyl compound when separated by chromatographed had a specific rotation of $[\alpha]_D^{20}$ = + 14° (c = 0.5% in chloroform).

EXAMPLE 4

B isomer of (17R) 7α-n-propyl-2-oxidospiro-($\Delta^4$-androstene-17,5'-[1',2']-oxathiolane)-3-one STEP A: A isomer of 17-tetrahydropyranyloxy-21-tertbutylsulfinyl-$\Delta^{4,6}$-(17α)-pregnadiene-3-one 0.25 g of p-toluene sulfonic acid monohydrate was added to a mixture of 5 g of the A isomer of 21-tertbutylsulfinyl-$\Delta^{4,6}$-(17α)-pregnadiene-17-ol-3-one, 50 ml of 3,4-dihydro (2H) pyran and 150 ml of tetrahydrofuran and the mixture was stirred for 16 hours at room temperature. The mixture was washed with an aqueous solution saturated with sodium bicarbonate and the organic phase was dried and evaporated to dryness. The residue was chromatographed over silica gel and was eluted with a 4-1 chlorform-ethyl acetate mixture to otain 5.13 g of amorphous isomer A of 17-tetrahydropyranyloxy-21-tertbutylsulfinyl-$\Delta^{4,6}$-(17α)-pregnadiene-3-one.

STEP B: A isomers of 7α-n-propyl-21-tertbutylsulfinyl-$\Delta^4$-(17α)-pregnene-17-ol-3-one and 7β-n-propyl-21-tertbutylsulfinyl-$\Delta^4$-(17α)-pregnene-17-ol-3-one 0.25 g of cuprous chloride were added at −30° C to a mixture of 33.5 ml of a solution of 0.92 M of n-propyl magnesium bromide in ethyl ether, 33.5 ml of ether and 33.5 ml of tetrahydrofuran and was stirred for 30 minutes. A solution of 5.13 g of the product of Step A in 30 ml of tetrahydrofuran was added thereto over 30 minutes and then 30 ml of 6N hydrochloric acid were added. The mixture was stirred for 30 minutes at room temperature and the organic phase was dried and evaporated to dryness. The residue was chromatographed over silica gel and was eluted with a 4-1 chloroform-acetone mixture to obtain 1.01 g of the A isomer of 7α-n-propyl-21-tertbutylsulfinyl-$\Delta^4$-(17α)-pregnene-17-ol-3-one melting at 240° C and 2.47 g of the A isomer of 7β-n-propyl-21-tertbutylsulfinyl-$\Delta^4$-(17α)-pregnene-17-ol-3-one melting at 232° C.

STEP C: B isomer of 7α-n-propyl-2'-oxidospiro-($\Delta^4$-androstene-17,5'-[1',2']-oxathiolane)-3-one Using the procedure of Step C of Example 2, the A isomer of Step B melting at 240° C was reacted to obtain the B isomer of 7α-n-propyl-2'-oxidospiro-($\Delta^4$-androstene-17,5'-[1',2']-oxathiolane)-3-one melting at 190° C and having a specific rotation $[\alpha]_D^{20}$ = + 2.5° ± 0.5° (c = 1% in chloroform).

EXAMPLE 5

B isomer of (17R) 7α-n-propyl-2'-oxidospiro-(Δ⁴-androstene-17,5'-[1',2']-oxathiolane)-3-one 7α-n-propyl-Δ⁴-androstene-17β-ol-3-one [Steroids, Vol. 27 (1976), p.759] was oxidized with Heilbron's reagent (270 g of chromic acid, 36N sulfuric acid + water for 1 liter) to obtain 7α-n-propyl-Δ⁴-androstene-3,17-dione melting at 192° C. The said product was treated with a mixture of ethyl orthoformate, absolute ethanol and p-toluene sulfonic acid to obtain 3-ethoxy-7α-n-propyl-Δ³,⁵-androstadiene-17-one. The latter was treated by the process of Example 2 to form the B isomer of (17R) 7α-n-propyl-2'-oxidospiro-(Δ⁴-androstene-17,5'-[1',2']-oxathiolane)-3-one identical to the product of Example 4.

EXAMPLE 6

Tablets were prepared from 50 mg of the 6β, 7β-isomer of Example 1 and sufficient excipient of talc, starch and magnesium stearate to obtain a final weight.

PHARMACOLOGICAL DATA

A. Antialdosterone Activity

Male rats of the Sprague-Dawley strain weighing about 180 g were surrenalectomized and at that moment, the rats received with drinking water a physiological serum. After 31 hours, the animals did not receive food or drink and then they received drinking water containing 5% glucose. At the end of 47 hours, the rats received orally either the B isomer of (17R) 6β, 7β-methylene-2'-oxidospiro-(Δ⁴-androstene-17,5'-[1',2']-oxathiolane)-3-one (product A), the B isomer of (17R) 6α, 7α-methylene-2'-oxidospiro-(Δ⁴-androstene-17,5'-[1',2']-oxathiolane)-3-one (product B) or the B isomer of (17R) 7α-methyl-2'-oxidospiro-(Δ⁴-androstene-17,5'-[1',2']-oxathiolane)-3-one (product C) in the form of a solution or suspension in 0.25% carboxymethylcellulose. One hour after the said oral administration, the animals received a hydrosaline overdose by intraperitoned administration of 5 ml of a 9% physiological serum per 100 g of body weight and 1 μg/kg of a 2.5% alcoholic solution of aldosterone monoacetate by subcutaneous administration. The animals were placed in diuresis cages without food or drink for 4 hours and at the end of 4 hours, a forced miction was caused by pressure on the bladder. The volume of urine was brought to 50 ml and the amount of sodium and potassium was determined with an autoanalyser. The results are expressed as a percentage of inhibition of the activity of 1 μg/kg of aldosterone monoacetate administered subcutaneously against the ratio of $$\frac{\text{sodium concentration}}{\text{potassium concentration}}$$

of the surrenalectomized rats in Table I.

TABLE I

| Product | Oral dose in mg/kg | % inhibition |
|---|---|---|
| A | 5 | 25 |
| B | 5 | 19 |
| C | 5 | 22 |

B. Affinity for androgenic receptors

The test used was the hormonal receptor test described by Raynaud et al [J. Ster. Biochem., Vol. 6 (1975), p. 615-622] in which the prostate was removed from male rats castrated 24 hours earlier and was homogenized in a buffer: 10 millimole tromethamine, saccharose 0.25M, HCl for pH of 7.4. The homogenate was centrifuged at 105,000g for one hour and the surnageant liquid or "cytosol" was then adjusted to obtain a dilution of 1/5 (weight/volume). The cytosol with a fixed concentration of tritiated 17α-methyl-Δ⁴,⁹,¹¹-estratriene-17β-ol-3-one (designated as tritiated product R) was incubated at 0° C for 2 hours, in the presence or absence of increasing concentration of the same cold product (designated as cold product R), of testosterone or of the test products. At the end of 2 hours, the radioactivity of tritiated product tied to the receptor was determined by the adsorption technique of carbondextran (1.25% to 0.625%).

The curves representing the percentages of tritiated product R tied with respect to the log of the concentration of the cold product R, testosterone or the test products added and the I₅₀ straight line parallel to axis of the abcisses and the ordinate of which is $$\frac{B}{T} = \frac{B/T \max. + B/T \min.}{2}$$

were drawn. B/T max. is the percentage of tritiated product R bound when no product was added and B/T min. is the percentage of tritiated product R bound when the mazimum quantity of cold product R is added. The intersections of line I₅₀ and the curves permit the determination of the CT and CX values. CT is the concentration of cold testosterone which inhibits by 50% the fixation of tritiated product R and CX is the concentration of test product which inhibits by 50% the fixation of tritiated product R. The relative affinity of the test product or RLA is determined by the formula $$RLA = 100 \times CT/CX$$

and the results are reported in Table II.

TABLE II

| Test Product | RLA |
|---|---|
| Testosterone | 100 |
| A | 0 |
| C | 3.6 |

The results show that products A and C possess little or no affinity for androgen receptors.

Various modification of the products and processes of the invention may be made without departing from the spirit or scope thereof and it is to be understood that the invention is intended to be limited only as defined in the appended claims.

We claim:

1. A compound selected from the group consisting of 17-spirosultines and their corresponding γ-hydroxy acids of the formula

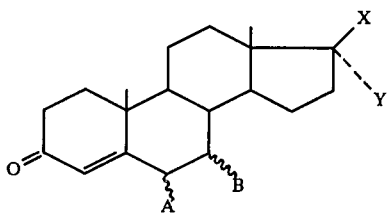

wherein A is hydrogen and B is alkyl of 1 to 4 carbon atoms in the α- or β-position or A and B form a methylene group in the 6α, 7α- or 6β, 7β-position and X and Y form a group of the formula

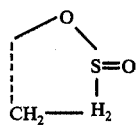

or X is OH and Y is

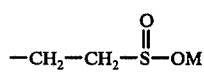

and M is selected from the group consisting of hydrogen, —NH$_4$ and an alkali metal cation.

2. A compound of claim 1 wherein X an Y form a group

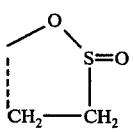

3. A compound of claim 1 wherein X is —OH and Y is

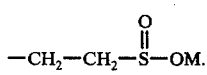

4. A compound of claim 1 wherein A and B are methylene in the 6α,7α- or 6β, 7β-position.

5. A compound of claim 1 wherein A is hydrogen and B is alkyl of 1 to 4 carbon atoms in the 7α-position.

6. A compound of claim 5 wherein B is methyl.

7. A compound of claim 1 selected from the group consisting of (17R) 6β, 7β-methylene-2'-oxidospiro-(Δ$^4$-androstene-17,5'-[1',2']-oxathiolane)-3-ones, (17R) 6α, 7α-methylene-2'-oxidospiro-(Δ$^4$-androstene-17,5'-[1',2']-oxathiolane)-3-ones, (17R) 7α-methyl-2'-oxidospiro-(Δ$^4$-androstene-17,5'-[1',2']-oxathiolane)-3-ones, (17R) 7β-methyl-2'-oxidospiro-(Δ$^4$-androstene-17,5'-[1',2']-oxathiolane)-3-ones and (17R) 7α-n-propyl-2'-oxidospiro-(Δ$^4$-androstene-17,5'-[1',2']-oxathiolane)-3-ones.

8. A process for the preparation of a compound of claim 2 comprising reacting a compound of the formula

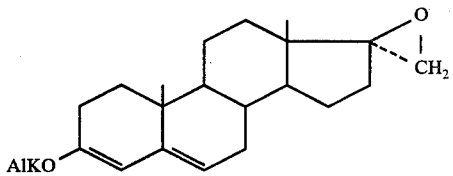

wherein AlK is alkyl of 1 to 4 carbon atoms with methyl tert. butylsulfoxide in the presence of n-butyllithium to obtain a compound of the formula

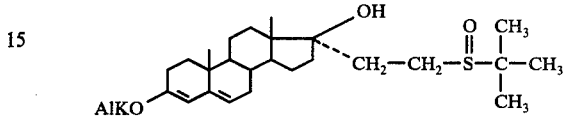

in the form of a mixture of diastereoisomers A and B about the sulfur atom, which may be separated if desired, reacting the latter with a dehydrogenation agent to form a compound of the formula

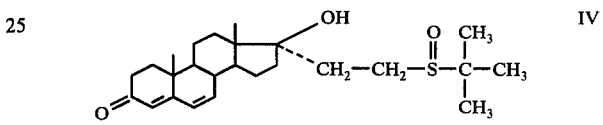

in the form of a mixture of diastereoisomers A and B which may be separated or as the individual isomer and either reacting the latter with a member of the group consisting of trimethyl sulfonium iodide and trimethylsulfoxonium iodide in the presence of a strong base to obtain a compound of the formula

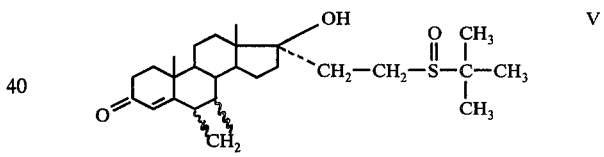

in the form of a mixture of 6α, 7α- and 6β, 7β-isomers which may be separated if desired or reacting the compound of formula IV with a dialkylcuprolithium of the formula

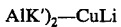

wherein AlK' is alkyl of 1 to 4 carbon atoms to form a compound of the formula

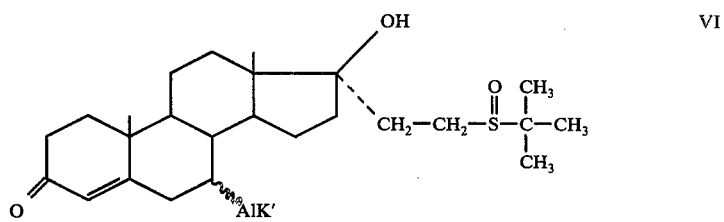

in the form of a mixture of the 7α- and 7β-isomers which may be separated if desired and then reacting a compound of formula V or VI with a member of the group consisting of N-chlorosuccinimide and N-bromosuccinimide to form a compound of claim 2.

9. A process for the preparation of a compound of the formula

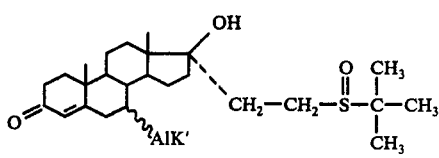

wherein AlK' is alkyl of 1 to 4 carbon atoms comprising reacting a compound of the formula

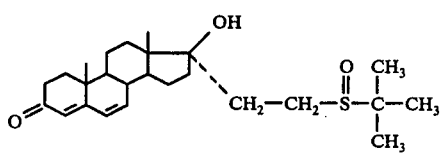

in the form a mixture of the diasteroisomers or as individual diastereoisomer with an AlK'-Mg-X wherein X is halogen in the presence of a cuprous salt to obtain the desired compound in the form of a mixture of the 7α- and 7β-isomers.

10. A process for the preparation of a compound of claim 3 comprising reacting a compound of claim 2 with a member of the group consisting of ammonium hydroxide and alkali metal hydroxide to obtain the desired compound which may be treated with an acid to obtain the corresponding acid which in turn may be treated with an alkali metal base to obtain the corresponding alkali metal salt.

11. A process for the preparation of a compound of claim 2 wherein A is hydrogen and B is alkyl of 1 to 4 carbon atoms comprising the steps of reacting a compound of the formula

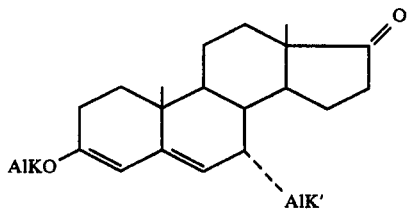

wherein Alk and Alk' are alkyl of 1 to 4 carbon atoms with trimethylsulfonium iodide or trimethylsulfoxonium iodide in the presence of a strong base to obtain a compound of the formula

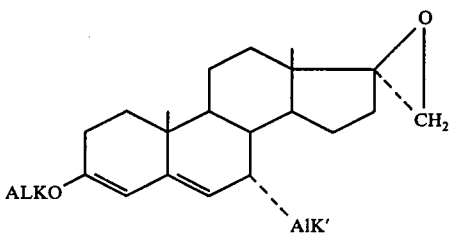

and reacting the latter with methyl tert.-butyl sulfoxide in the presence of n-butyllithium and then with an acid to obtain a compound of the formula

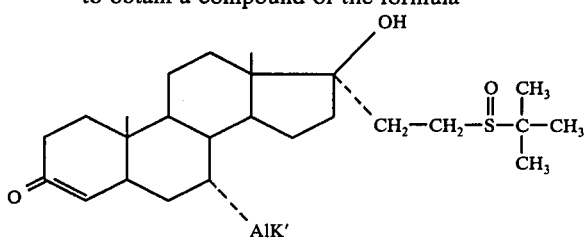

in the form of a mixture of the diastereoisomers about the sulfur atoms, which may be separated if desired, and the said product is reacted with thionyl chloride, N-chlorosuccinimide or N-bromosuccinimide to obtain a compound of the formula

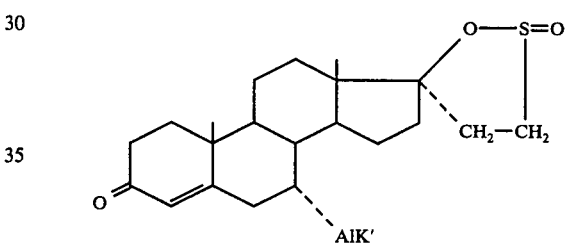

in the form of a diastereoisomer or a mixture of diastereoisomers which can be separated if desired.

12. An antialdosterone composition an antialdosteronically effective amount of at least one compound of claim 1 and an inert pharmaceutical carrier.

13. A composition of claim 12 wherein the compound is selected from the group consisting of (17R) 6β, 7β-methylene-2'-oxidospiro-(Δ⁴-androstene-17,5'-[1',2']-oxathiolane)-3-ones, (17R) 6α, 7α-methylene-2'-oxidospiro-(Δ⁴-androstene-17,5'-[1',2']-oxathiolane)-3-ones, (17R) 7α-methyl-2'-oxidospiro-(Δ⁴-androstene-17,5'-[1',2']-oxathiolane)-3-ones, (17R) 7β-methyl-2'-oxidospiro-(Δ⁴-androstene-17,5'-[1',2']-oxathiolane)-3-ones and (17R) 7α-n-propyl-2'-oxidospiro-(Δ⁴androstene-17,5'-[1',2']-oxathiolane)-3-ones.

14. A method of relieving hypertension and cardiac insufficiencies in warm-blooded animals comprising administering to warm-blooded animals a hypotensively effective amount of at least one compound of claim 1.

15. The method of claim 14 wherein the compound is selected from the group consisting of (17R) 6β, 7β-methylene-2'-oxidospiro-(Δ⁴-androstene-17,5'-[1',2']-oxathiolane)-3-ones, (17R) 6α, 7α-methylene-2'-oxidospiro-(Δ⁴-androstene-17,5'-[1',2']-oxathiolane)-3-ones, (17R) 7α-methyl-2'-oxidospiro-(Δ⁴-androstene-17,5'-[1',2']-oxathiolane)-3-ones, (17R) 7β-methyl-2'-oxidospiro-(Δ⁴-androstene-17,5'-[1',2']-oxathiolane)-3-ones and (17R) 7α-n-propyl-2'-oxidospiro-(Δ⁴-androstene-17,5'-[1',2']-oxathiolane)-3-ones.

* * * * *